US012214345B2

United States Patent
Fuller et al.

(10) Patent No.: US 12,214,345 B2
(45) Date of Patent: *Feb. 4, 2025

(54) MULTI-STAGE ORAL-FLUID TESTING DEVICE WITH CAP CONTAINING PLUNGER FOR ORAL-FLUID RELEASE FROM COLLECTION SPONGE

(71) Applicant: Premier Biotech, LLC, Minneapolis, MN (US)

(72) Inventors: Kevin S. Fuller, Chaska, MN (US); Wayde J. Altendorf, Hickson, ND (US); Todd Bailey, Shorewood, MN (US)

(73) Assignee: Premier Biotech, LLC, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/403,013

(22) Filed: Aug. 16, 2021

(65) Prior Publication Data

US 2022/0023858 A1     Jan. 27, 2022

Related U.S. Application Data

(63) Continuation of application No. 16/050,921, filed on Jul. 31, 2018, now Pat. No. 11,090,648, which is a
(Continued)

(51) Int. Cl.
*G01N 33/487*     (2006.01)
*A61B 10/00*     (2006.01)
*B01L 3/00*     (2006.01)

(52) U.S. Cl.
CPC ........ *B01L 3/5023* (2013.01); *A61B 10/0051* (2013.01); *B01L 3/5029* (2013.01);
(Continued)

(58) Field of Classification Search
CPC .... G01N 33/48; G01N 33/487; G01N 1/4077; B01L 3/00; B01L 3/5023; B01L 3/5029; B01L 3/0272; A61B 10/0051
(Continued)

(56) References Cited

U.S. PATENT DOCUMENTS 3,616,263 A   *   10/1971   Anandam ............... C12M 29/00
                                                          435/304.2
3,704,206 A   *   11/1972   Freake ...................... C12Q 1/04
                                                          435/287.8
(Continued)

FOREIGN PATENT DOCUMENTS

| JP | 63-293439 | 11/1988 |
|---|---|---|
| WO | 03060479 A3 | 10/2003 |
| WO | 2010101564 A1 | 9/2010 |

OTHER PUBLICATIONS

Partial European Search Report for European Patent Application No. 19188518.5 dated May 15, 2020; 9 pgs.

*Primary Examiner* — Arlen Soderquist
(74) *Attorney, Agent, or Firm* — Nelson Mullins Riley & Scarborough LLP

(57) ABSTRACT

In an embodiment, the claimed invention includes an oral-fluid collection and testing device that. is simple to operate. The device includes a body assembly and a cap assembly that are easy to handle by a user. A collection sponge projects from an end of the body assembly for absorbing the oral fluid of a donor, A cap assembly is easily aligned with the body assembly by way of visual alignment indicators on both the body and the cap. Once the cap is aligned with the body, a user simply pushes the cap onto the 'body, which causes a first stage fluid, flow. More specifically, a buffer fluid is released from the cap and mixes with the oral fluid collected on the sponge—After waiting a short time* the cap is rotated, then pushed again, causing a second-stage fluid (Continued)

flow in which the sponge is compressed such that the buffer fluid/oral fluid exits the sponge and flows toward a. pair of test strips. A user can then easily view the test results by observing a visual indication, such as a color change of the test strips through a viewing window.

23 Claims, 13 Drawing Sheets

Related U.S. Application Data continuation of application No. 14/893,461, filed as application No. PCT/US2014/039607 on May 27, 2014, now Pat. No. 10,035,146.

(60) Provisional application No. 61/827,328, filed on May 24, 2013.

(52) U.S. Cl.
CPC .... *G01N 33/487* (2013.01); *A61B 2010/0006* (2013.01); *A61B 2010/0009* (2013.01); *B01L 2200/025* (2013.01); *B01L 2200/0684* (2013.01); *B01L 2200/10* (2013.01); *B01L 2300/042* (2013.01); *B01L 2300/046* (2013.01); *B01L 2300/047* (2013.01); *B01L 2300/0663* (2013.01); *B01L 2300/069* (2013.01); *B01L 2300/0825* (2013.01); *B01L 2300/0864* (2013.01); *B01L 2400/0406* (2013.01); *B01L 2400/0478* (2013.01)

(58) Field of Classification Search
USPC ................ 422/408, 413, 417, 419–420, 430; 436/94, 164, 169
See application file for complete search history.

(56) References Cited

U.S. PATENT DOCUMENTS

| | | | | |
|---|---|---|---|---|
| 3,715,189 A * | 2/1973 | Nighohossian | ......... | B01L 3/502 422/430 |
| 3,815,580 A * | 6/1974 | Oster | ..................... | A61B 10/02 600/572 |
| 3,918,435 A * | 11/1975 | Beall | ....................... | A61F 13/38 600/572 |
| 3,968,872 A * | 7/1976 | Cavazza | ............. | B65D 51/285 604/416 |
| 4,014,322 A * | 3/1977 | Shah | ..................... | A61B 10/007 422/50 |
| 4,257,427 A * | 3/1981 | Bucalo | .............. | A61B 10/0045 435/309.1 |
| 4,635,488 A * | 1/1987 | Kremer | .................... | G01N 1/10 600/584 |
| 4,682,689 A * | 7/1987 | Pereira | ............... | B65D 81/3211 206/217 |
| 4,757,916 A * | 7/1988 | Goncalves | ......... | B65D 81/3211 222/153.07 |
| 4,770,853 A * | 9/1988 | Bernstein | ........... | G01N 33/5302 435/287.7 |
| 4,774,962 A * | 10/1988 | Hebel | ................ | A61B 10/0051 600/573 |
| 4,813,432 A * | 3/1989 | Saint-Amand | ........ | B01L 3/5029 600/572 |
| 4,898,293 A * | 2/1990 | Morel | ................ | B65D 81/3211 215/250 |
| 4,963,325 A * | 10/1990 | Lennon | ................... | B01L 3/508 422/430 |
| 4,976,379 A * | 12/1990 | Sloan | ....................... | B67B 7/26 222/153.07 |
| 4,982,875 A * | 1/1991 | Pozzi | ................ | B65D 81/3222 604/416 |
| 5,029,718 A * | 7/1991 | Rizzardi | ............ | B65D 55/0863 215/254 |
| 5,065,768 A * | 11/1991 | Coleman | .......... | A61B 5/150351 600/573 |
| 5,160,704 A * | 11/1992 | Schluter | ............... | G01N 33/491 422/535 |
| 5,211,182 A * | 5/1993 | Deutsch | ............. | A61B 10/0012 600/584 |
| 5,268,148 A * | 12/1993 | Seymour | ............ | A61B 10/0051 422/547 |
| 5,283,038 A * | 2/1994 | Seymour | ............ | A61B 10/0051 600/573 |
| 5,334,502 A * | 8/1994 | Sangha | ............... | A61B 10/0051 436/805 |
| 5,342,346 A * | 8/1994 | Honda | .................. | A61J 1/2089 604/82 |
| 5,352,410 A * | 10/1994 | Hansen | ................ | A61B 10/007 422/430 |
| 5,376,337 A * | 12/1994 | Seymour | ............ | A61B 10/0051 422/535 |
| 5,380,492 A * | 1/1995 | Seymour | ............... | B01L 3/5029 422/534 |
| 5,393,496 A * | 2/1995 | Seymour | ................ | B01L 3/502 422/534 |
| 5,494,646 A * | 2/1996 | Seymour | ............ | A61B 5/15142 435/287.7 |
| 5,830,410 A * | 11/1998 | Thieme | ............ | G01N 33/56988 422/430 |
| 5,846,487 A * | 12/1998 | Bennett, II | .............. | B01L 3/545 422/417 |
| 5,869,003 A * | 2/1999 | Nason | ....................... | G01N 1/02 422/430 |
| 5,922,614 A * | 7/1999 | Cesarczyk | ............... | G01N 1/02 422/411 |
| 5,981,300 A * | 11/1999 | Moll | ....................... | C12Q 1/04 436/811 |
| 5,985,675 A * | 11/1999 | Charm | ............ | G01N 33/54366 436/514 |
| 6,138,821 A * | 10/2000 | Hsu | ..................... | B65D 51/2828 215/DIG. 8 |
| 6,140,136 A * | 10/2000 | Lee | ....................... | G01N 33/558 435/7.1 |
| 6,148,996 A * | 11/2000 | Morini | ................. | B65D 51/285 215/DIG. 8 |
| 6,149,866 A * | 11/2000 | Luotola | ............. | B65D 51/2871 206/217 |
| 6,150,178 A * | 11/2000 | Cesarczyk | ........... | B01L 3/5029 422/412 |
| 6,197,254 B1 * | 3/2001 | Silver | .................... | G01N 21/76 422/52 |
| 6,328,931 B1 * | 12/2001 | Silver | ................... | G01N 21/76 422/417 |
| 6,372,511 B1 * | 4/2002 | Silver | .................... | G01N 21/76 250/361 C |
| 6,416,715 B1 * | 7/2002 | Gambert | .......... | A61B 10/0051 422/513 |
| 6,464,939 B1 * | 10/2002 | Bachand | ................ | B08B 1/003 600/572 |
| 6,468,474 B2 * | 10/2002 | Bachand | ................ | B08B 1/003 600/572 |
| 6,489,172 B1 * | 12/2002 | Bachand | ............ | A61B 10/0051 600/572 |
| 6,527,110 B2 * | 3/2003 | Moscovitz | ................ | B67B 7/26 215/DIG. 8 |
| 6,634,243 B1 * | 10/2003 | Wickstead | .............. | B01L 3/502 422/417 |
| 6,641,782 B1 * | 11/2003 | Mauchan | ............ | G01N 21/76 422/52 |
| 6,716,392 B1 * | 4/2004 | Putcha | .................. | B01L 3/5082 252/186.25 |
| 6,820,740 B1 * | 11/2004 | Spector | ............. | B65D 51/2828 215/250 |
| 6,821,788 B2 * | 11/2004 | Cesarczyk | ......... | A61B 10/0045 436/169 |
| 6,875,185 B2 * | 4/2005 | Wong | .................... | A61B 5/145 600/584 |

(56) References Cited

U.S. PATENT DOCUMENTS

| | | | |
|---|---|---|---|
| 7,029,627 B2* | 4/2006 | Alley | B01L 3/5029 422/50 |
| 7,249,690 B2* | 7/2007 | Smith | B65D 51/2835 222/153.05 |
| 7,270,959 B2* | 9/2007 | Hudak | B01L 3/502 422/537 |
| 7,282,181 B2* | 10/2007 | Hudak | A61B 10/0051 422/549 |
| 7,378,054 B2* | 5/2008 | Karmali | B01L 3/5021 422/410 |
| 7,387,899 B1* | 6/2008 | D'Angelo | A61B 10/0051 435/287.7 |
| 7,587,793 B2* | 9/2009 | Sangha | A61B 90/96 422/550 |
| 7,618,591 B2* | 11/2009 | Slowey | A61B 10/02 422/412 |
| 7,666,667 B2* | 2/2010 | Yong | B01L 3/5029 435/309.1 |
| 7,695,953 B2* | 4/2010 | Gould | A61B 10/007 436/514 |
| 7,741,103 B2* | 6/2010 | Guirguis | G01N 33/9486 436/514 |
| 7,749,771 B2* | 7/2010 | Burgess-Cassler | G01N 33/54366 436/805 |
| 7,824,344 B1* | 11/2010 | Altschul | A61B 10/0051 435/805 |
| 7,850,922 B2* | 12/2010 | Gallagher | G01N 1/10 436/178 |
| 7,854,895 B2* | 12/2010 | Gallagher | A61B 10/0096 436/177 |
| 7,879,293 B2* | 2/2011 | Niedbala | B01L 3/5023 422/501 |
| 7,879,623 B2* | 2/2011 | Guirguis | A61B 10/0051 436/514 |
| 7,915,032 B2* | 3/2011 | Ostrowski | B01L 3/5029 435/287.7 |
| 7,951,032 B2* | 5/2011 | Yagasaki | F16H 55/38 474/260 |
| 8,025,851 B2* | 9/2011 | Slowey | A61B 10/0051 600/576 |
| 8,273,305 B2* | 9/2012 | Slowey | A61B 10/02 600/573 |
| 8,522,968 B2* | 9/2013 | Middleman | A47G 21/00 206/568 |
| 8,642,323 B2* | 2/2014 | Sharpin | C12M 41/36 435/287.1 |
| 8,673,239 B2* | 3/2014 | Niedbala | B01L 3/5029 422/430 |
| 8,871,155 B2* | 10/2014 | Wu | B01L 3/5023 422/402 |
| 8,883,489 B2* | 11/2014 | Pang | G01N 33/5302 435/283.1 |
| 8,940,527 B2* | 1/2015 | Guirguis | G01N 33/94 436/514 |
| 9,821,938 B2* | 11/2017 | Valentine | B65D 51/2821 |
| 10,035,146 B2* | 7/2018 | Fuller | A61B 10/0051 |
| 11,090,648 B2* | 8/2021 | Fuller | G01N 33/487 |
| 2001/0046687 A1* | 11/2001 | DiCesare | G01N 21/763 435/8 |
| 2002/0001539 A1* | 1/2002 | DiCesare | B01L 3/5029 422/174 |
| 2002/0004019 A1* | 1/2002 | Bachand | B08B 1/003 435/287.7 |
| 2002/0066677 A1* | 6/2002 | Moscovitz | B65D 81/3211 206/219 |
| 2002/0146346 A1* | 10/2002 | Konecke | G01N 33/94 422/417 |
| 2003/0064526 A1* | 4/2003 | Niedbala | B01L 3/5029 600/584 |
| 2003/0133847 A1* | 7/2003 | Hagen | G01N 33/48757 422/430 |
| 2003/0190259 A1* | 10/2003 | Alley | A61B 10/0051 422/411 |
| 2003/0209653 A1* | 11/2003 | Feldsine | G01N 21/76 250/214 R |
| 2004/0005246 A1* | 1/2004 | Efthimiadis | B01L 3/563 422/534 |
| 2004/0116869 A1* | 6/2004 | Heinz | A61M 5/347 604/181 |
| 2005/0106753 A1* | 5/2005 | Wu | B01L 3/0272 436/180 |
| 2005/0202568 A1* | 9/2005 | Tung | G01N 33/48714 422/400 |
| 2006/0013738 A1* | 1/2006 | Ramsey | A61B 10/0045 422/400 |
| 2006/0018800 A1* | 1/2006 | Slowey | B01L 3/5029 422/412 |
| 2006/0057027 A1* | 3/2006 | Hudak | A61B 10/0051 422/549 |
| 2006/0074347 A1* | 4/2006 | Eguchi | B01L 3/5029 600/572 |
| 2006/0121548 A1* | 6/2006 | Robbins | C12Q 1/34 435/287.1 |
| 2006/0292034 A1* | 12/2006 | Gould | B01L 3/5023 422/400 |
| 2006/0292035 A1* | 12/2006 | Gould | A61B 10/0051 422/417 |
| 2007/0031914 A1* | 2/2007 | Zhu | C12Q 1/6883 435/25 |
| 2007/0128070 A1* | 6/2007 | Wu | A61B 10/0051 422/400 |
| 2007/0167910 A1* | 7/2007 | Tennican | A61M 5/31596 604/110 |
| 2007/0239068 A1* | 10/2007 | Rasch-Menges | A61B 5/14514 600/576 |
| 2007/0239069 A1* | 10/2007 | Guirguis | G01N 33/5302 600/584 |
| 2007/0244368 A1* | 10/2007 | Bayloff | A61B 10/0045 600/300 |
| 2008/0058676 A1* | 3/2008 | Yong | A61B 10/0051 600/572 |
| 2008/0058677 A1* | 3/2008 | Yong | A61B 10/0045 600/573 |
| 2008/0194041 A1* | 8/2008 | Guirguis | A61B 10/0051 422/400 |
| 2008/0286831 A1* | 11/2008 | Liang | A61B 10/0096 435/288.7 |
| 2009/0117665 A1* | 5/2009 | Tung | G01N 33/48714 422/68.1 |
| 2009/0155124 A1* | 6/2009 | Wan | B01L 3/502 422/68.1 |
| 2009/0181451 A1* | 7/2009 | Slowey | B01L 3/5029 435/287.7 |
| 2009/0197283 A1* | 8/2009 | Gold | B01L 3/5029 435/7.9 |
| 2009/0226883 A1* | 9/2009 | Wu | B01L 3/5023 435/287.7 |
| 2009/0306543 A1* | 12/2009 | Slowey | A61B 10/0051 600/576 |
| 2010/0081165 A1* | 4/2010 | Pasmore | C12M 37/06 435/31 |
| 2010/0129922 A1* | 5/2010 | Gold | G01N 33/54386 422/400 |
| 2010/0140209 A1* | 6/2010 | Valentine | B65D 51/2835 215/329 |
| 2010/0310426 A1* | 12/2010 | Campbell | B01L 3/563 141/330 |
| 2011/0165020 A1* | 7/2011 | Tryggvason | A61M 39/162 137/15.01 |
| 2011/0165024 A1* | 7/2011 | Wu | B01L 3/5023 422/69 |
| 2011/0212002 A1* | 9/2011 | Curry | A61B 10/0096 422/430 |
| 2011/0230737 A1* | 9/2011 | Duda | A61B 5/415 600/562 |
| 2011/0268626 A1* | 11/2011 | Slowey | A61B 10/0051 422/402 |

(56) References Cited

U.S. PATENT DOCUMENTS

| | | | | |
|---|---|---|---|---|
| 2012/0067144 | A1* | 3/2012 | Slowey | A61B 10/0051 |
| | | | | 73/864.73 |
| 2012/0094303 | A1* | 4/2012 | Engel | G01N 33/558 |
| | | | | 435/7.1 |
| 2012/0282154 | A1* | 11/2012 | Slowey | G01N 21/8483 |
| | | | | 422/401 |
| 2012/0325721 | A1* | 12/2012 | Plante | A61B 10/0051 |
| | | | | 422/550 |
| 2013/0331810 | A1* | 12/2013 | Bazala | A61J 1/1412 |
| | | | | 220/737 |
| 2014/0004548 | A1* | 1/2014 | Gordon | G01N 21/763 |
| | | | | 422/549 |
| 2014/0227796 | A1* | 8/2014 | Gold | G01N 33/54366 |
| | | | | 422/69 |
| 2015/0182156 | A1* | 7/2015 | Engbersen | G01N 33/54366 |
| | | | | 435/7.94 |
| 2015/0212081 | A1* | 7/2015 | Catteruccia | B01L 3/5029 |
| | | | | 435/5 |
| 2015/0285741 | A1* | 10/2015 | Bonecker | B01L 3/508 |
| | | | | 436/166 |
| 2016/0121322 | A1* | 5/2016 | Fuller | B01L 3/5023 |
| | | | | 422/417 |

\* cited by examiner

MULTI-STAGE ORAL-FLUID TESTING DEVICE WITH CAP CONTAINING PLUNGER FOR ORAL-FLUID RELEASE FROM COLLECTION SPONGE

CROSS-REFERENCE TO RELATED APPLICATIONS

This application is a continuation application of U.S. patent application Ser. No. 16/050,921 filed Jul. 31, 2018, now U.S. Pat. No. 11,090,648, which is a continuation application of U.S. patent application Ser. No. 14/893,461 filed Nov. 23, 2105, now U.S. Pat. No. 10,035,146, which is a national stage filing of PCT/US14/39607 filed May 27, 2014 which claims the benefit of Provisional Application Ser. No. 61/827,328 filed May 24, 2013.

FIELD OF THE INVENTION

The claimed invention relates to devices for collecting and testing oral fluid. In particular, the claimed invention relates to multi-stage oral fluid collection and testing of one or more substances.

BACKGROUND OF THE INVENTION

Bodily fluids are collected for various reasons, including diagnosing illness, simple therapeutic removal, determining pregnancy, confirming or establishing levels of therapeutic agents, determining drug abuse, and profiling DNA composition. Blood, urine, and saliva are among the commonly collected bodily fluids for some or all of these purposes. Among these, saliva has an advantage over other fluids for ease of collection. This is especially true for drugs-of-abuse-testing and for DNA testing.

Screening for drugs of abuse is performed by health professionals, law enforcement personnel, and government or private employers, among others. Substances of abuse that are commonly screened for include alcohol, cannabis, barbiturates, opioids, cocaine, amphetamines, and hallucinogens. For many such tests and testing environments, blood or urine collection is difficult, if not impossible, making saliva collection an appealing alternative. Saliva is less invasive to obtain than either blood or urine, and does not invoke privacy concerns to the same extent as does urine.

DNA testing is used for purposes of paternity, genealogy, disease susceptibility, and forensics, among others. Blood samples, buccal swabs, and saliva are commonly used for DNA tests. Collecting saliva is less invasive than collecting blood, and saliva collection can provide a larger, and therefore perhaps more reliable sample than buccal swabs.

Saliva samples are commonly collected by one of two methods: intra-oral sponge absorption and direct expectoration. An example of the first is U.S. Pat. No. 4,580,577 to O'Brien, et al., which discloses an absorbent mass that is masticated by the donor until saturated. The mass is placed in a squeezing device to expel saliva into a holding chamber, out of which a test aliquot can be removed. Sponge or sponge-like absorption methods are disclosed in numerous other patents, teaching variations such as added reagents, salivation promoters, preservatives, flavorings, chemical stabilizers, and a plurality of samples, among others.

However, such known saliva collection devices can be inconvenient to use, may be prone to leakage and contamination, and may yield inaccurate results due to user error.

SUMMARY OF THE INVENTION

Embodiments of the claimed invention solve many of the problems of known collection devices and test devices by providing convenient, easy to use combined collection and testing devices that accurately test for substances in a donor's oral fluids.

In an embodiment, the claimed invention includes an oral-fluid collection and testing device that is simple to operate. The device includes a body assembly and a cap assembly that are easy to handle by a user. A collection sponge projects from an end of the body assembly for absorbing the oral fluid of a donor. A cap assembly is easily aligned with the body assembly by way of visual alignment indicators on both the body and the cap. Once the cap is aligned with the body, a user simply pushes the cap onto the body, which causes a first stage fluid flow. More specifically, a buffer fluid is released from the cap and mixes with the oral fluid collected on the sponge. After waiting a short time, the cap is rotated, then pushed again, causing a second-stage fluid flow in which the sponge is compressed such that the buffer fluid/oral fluid exits the sponge and flows toward a pair of test strips. A user can then easily view the test results by observing a visual indication, such as a color change of the test strips through a viewing window.

In another embodiment, the claimed invention includes an oral collection and testing device that can test for the presence or absence of multiple substances in an oral fluid, and display the results to a user, during a single test operation. In such an embodiment, the testing device includes a pair of test strips secured in a pair of test strip channels beneath a pair of viewing windows. Buffered solution mixes centrally with the collected oral fluid, and flows to both test strips. A first test strip may test for a first substance, while a second test strip tests for a second substance, the first substance being different than the first substance.

In yet another embodiment, the claimed invention comprises a testing device with an improved flow path that enhances capillary rise, reduces splashing that could obscure viewing windows or suggest false results, and that ensures efficient venting without fluid leakage. A first stage flow path includes a plunger channel directing buffer fluid from a fluid container toward a collection sponge, where collected oral fluid is mixed with the buffer fluid. A second stage flow path includes a fluid reservoir adjacent the collection sponge, coupled to first and second test strip channels, holding first and second test strips, respectively. Bridges crossing the channels transversely may include projections on a top surface, and are configured to compress and secure portions of the test strips in their respective channels. The resulting restrictive nature of the bridges results in increased capillary rise and elimination of splashing in the vicinity of view windows. Each channel is in communication with a vent channel leading to a vent sponge, such that trapped air may be exhausted during operation of the device, but without fluid leakage.

Other embodiments, including methods of the claimed invention, are further described throughout the specification, figures, and claims herein.

BRIEF DESCRIPTION OF THE FIGURES

The invention can be understood in consideration of the following detailed description of various embodiments of the invention in connection with the accompanying drawings, in which.

DETAILED DESCRIPTION

Figure 1:
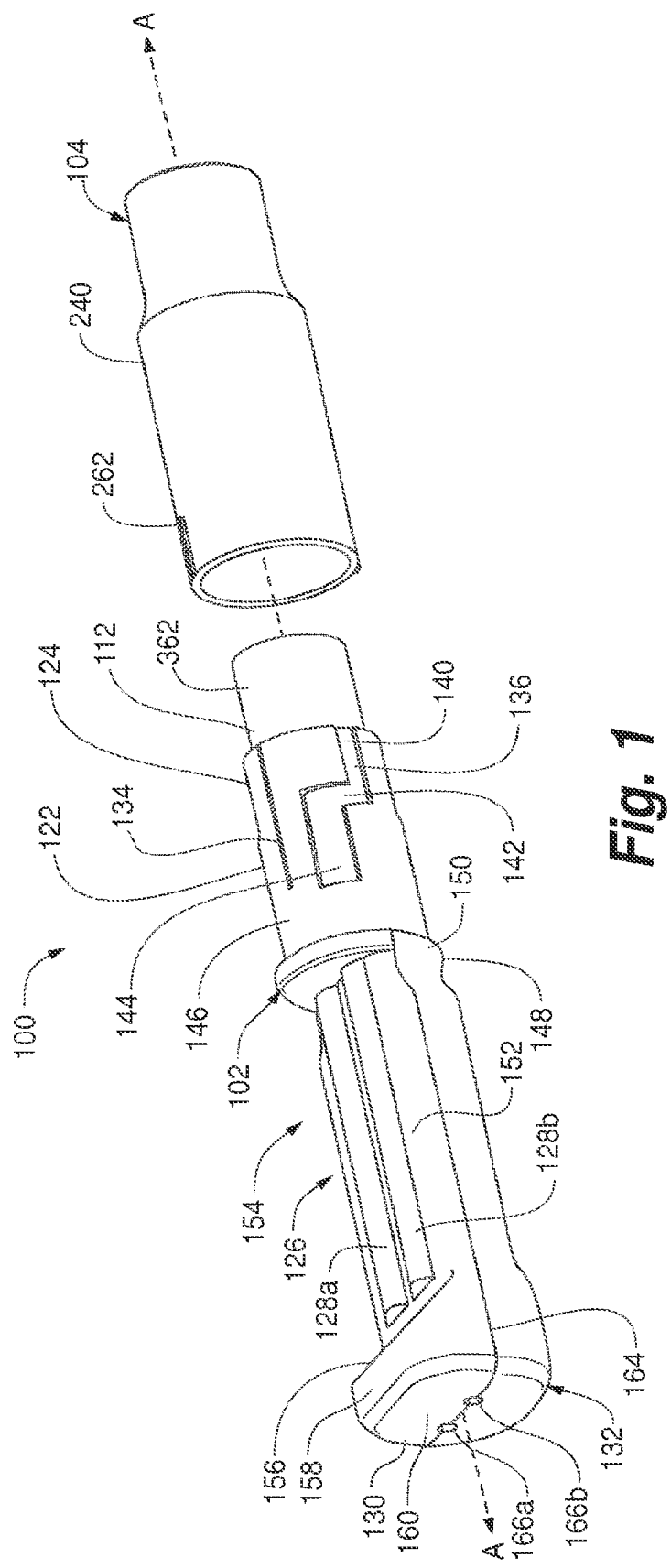
FIG. 1 is a perspective view of a multi-stage oral-fluid collecting and testing device, according to an embodiment.

Referring to FIG. 1, an embodiment of multi-stage oral-fluid collection and testing device 100 ("oral-fluid testing device" 100) is depicted. In an embodiment, oral-fluid testing device 100 includes collection-and-test body assembly 102 ("body assembly" 102) and cap assembly 104.

Figure 2:
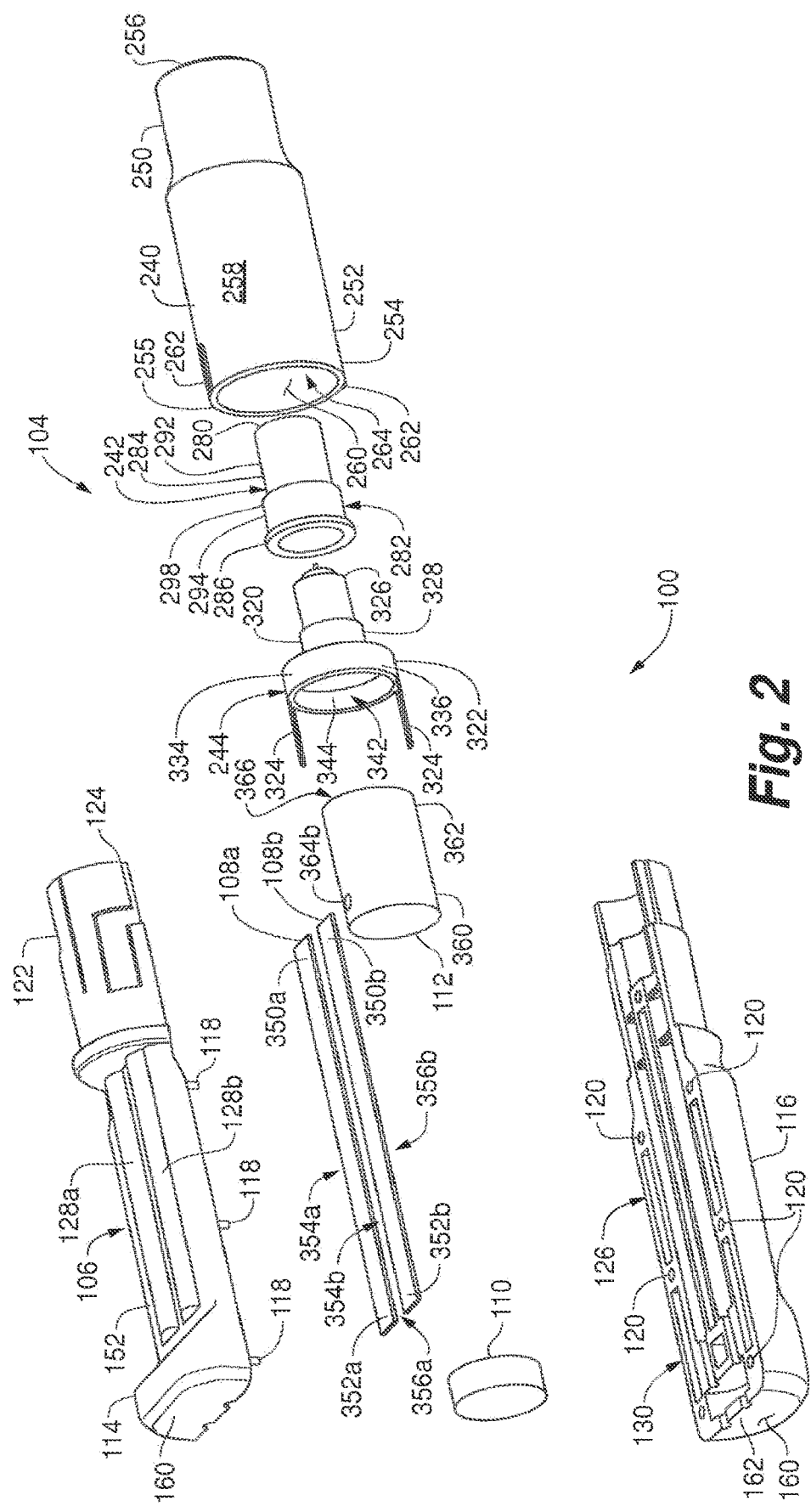
FIG. 2 is an exploded view of the testing device of FIG. 1.

Referring also to FIG. 2, oral-fluid testing device 100 is depicted in exploded view. In an embodiment, test body 102 includes body portion 106, test strips 108a and 108b, vent sponge 110, and oral-fluid collection sponge 112.

Body portion 106, as depicted, includes first, or upper, body portion 114, coupled to second, or lower, body portion 116. First body portion 114 may be coupled to second body portion 116 in any number of ways. In an embodiment, first body portion 114 includes multiple projections 118 extending outward and away from an edge of body portion 114. Second body portion 116 may include corresponding holes 120 adapted to receive projections 118. After assembling first body portion 114 to second body portion 116, the body portions may be sonically welded to secure the two body portions together. In other embodiments, projections 118 with holes 120 may form a snap fit. In further embodiments, adhesives may be also be used to join first body portion 114 to second body portion 116.

Body portion 106 may be generally cylindrical or tubular, and in some embodiments, adapted to be gripped by a user's hand. Body portion 106 may comprise any of a variety of materials, including various know injection molded polymers such as polycarbonate etc.

Body portion 106 also includes cap-engagement portion 122 at first or proximal end 124, viewing-window portion 126 with viewing windows 128a and 128b, and vent portion 130 at second or distal end 132.

Cap-engagement portion 122 is generally configured to fit into cap 104, and may define a generally cylindrical shape. In an embodiment, cap engagement portion 122 defines a plurality of grooves or channels, including visual-alignment grooves 134 and cap-guide channels 136, and plunger-guide channels 138 (see also FIGS. 7, 10, and 11).

When present, visual-alignment grooves 134 extend longitudinally, or axially, along a portion of the length of body 106, including cap engagement portion 122. Cap-engagement portion 122 may include first visual-alignment groove 134 in first body portion as depicted in FIGS. 1 and 2, and may include a second corresponding groove, not depicted in FIGS. 1 and 2, located opposite to 134 on second body portion 116. As will be explained further below, visual-alignment grooves 134 provide a visual marker for rotationally aligning body assembly 102 relative to cap 104. In other embodiments, visual-alignment grooves 134 may comprise other visual indicators, such as a projection (with mating with a slot in cap assembly 104), a printed line, or other such alignment indicator.

Figure 9:
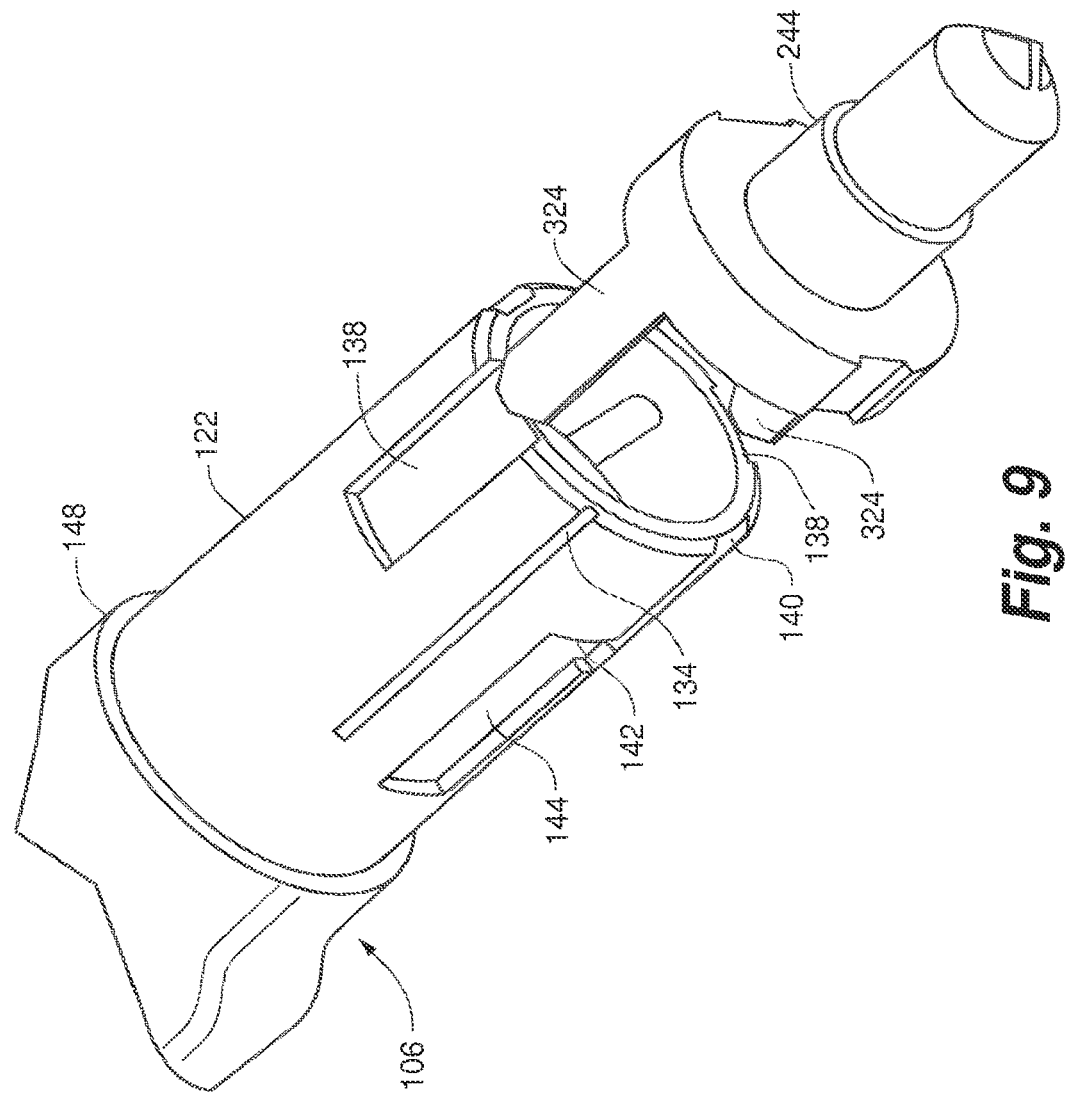
FIG. 9 is a perspective view of the body and plunger of FIG. 7, the plunger aligned with the body in second alignment position, after rotation, according to an embodiment.

In an embodiment, cap-engagement portion 122 defines one or more cap-guide channels 136. A first cap-guide channel 136 is depicted in FIGS. 1 and 2. A second plunger-guide channel 136 is depicted in FIG. 9 below. In an embodiment, cap-guide channel 136 defines a first channel portion 140, second channel portion 142, and third channel portion 144. First channel portion 140 and third channel portion 144 extend axially along an outside engagement surface 146 of cap-engagement portion 122, and are linked by radially-extending second channel portion 142. First channel portion 140 extends axially from an outermost edge of first end 124 toward second end 132. Third channel portion 144 also extends axially, and in an embodiment, parallel to, and offset from, first channel portion 140. In an embodiment, and as depicted, second channel portion 142 may be defined from portions of first and third channel portions 140 and 144 when such portions are adjacent one another.

Channel portions 140, 142, and 144 may define relatively shallow portions that in an embodiment do not define openings into an inside portion of body 106. In other embodiments, one or more channel portions 140, 142, and 144 may penetrate the wall of body 106 to define an opening into body 106.

In an embodiment, cap-engagement portion 122 includes a pair of cap-guide channels 136, though it will be understood that only one, or more than two cap-guide channels 136 may be defined by cap-engagement portion 122.

Rather than utilizing the push-rotate-push arrangement described above, a more traditional rotation only arrangement with cooperating threads; such may be helical channels of similar proportion to what is illustrated.

Figure 10:
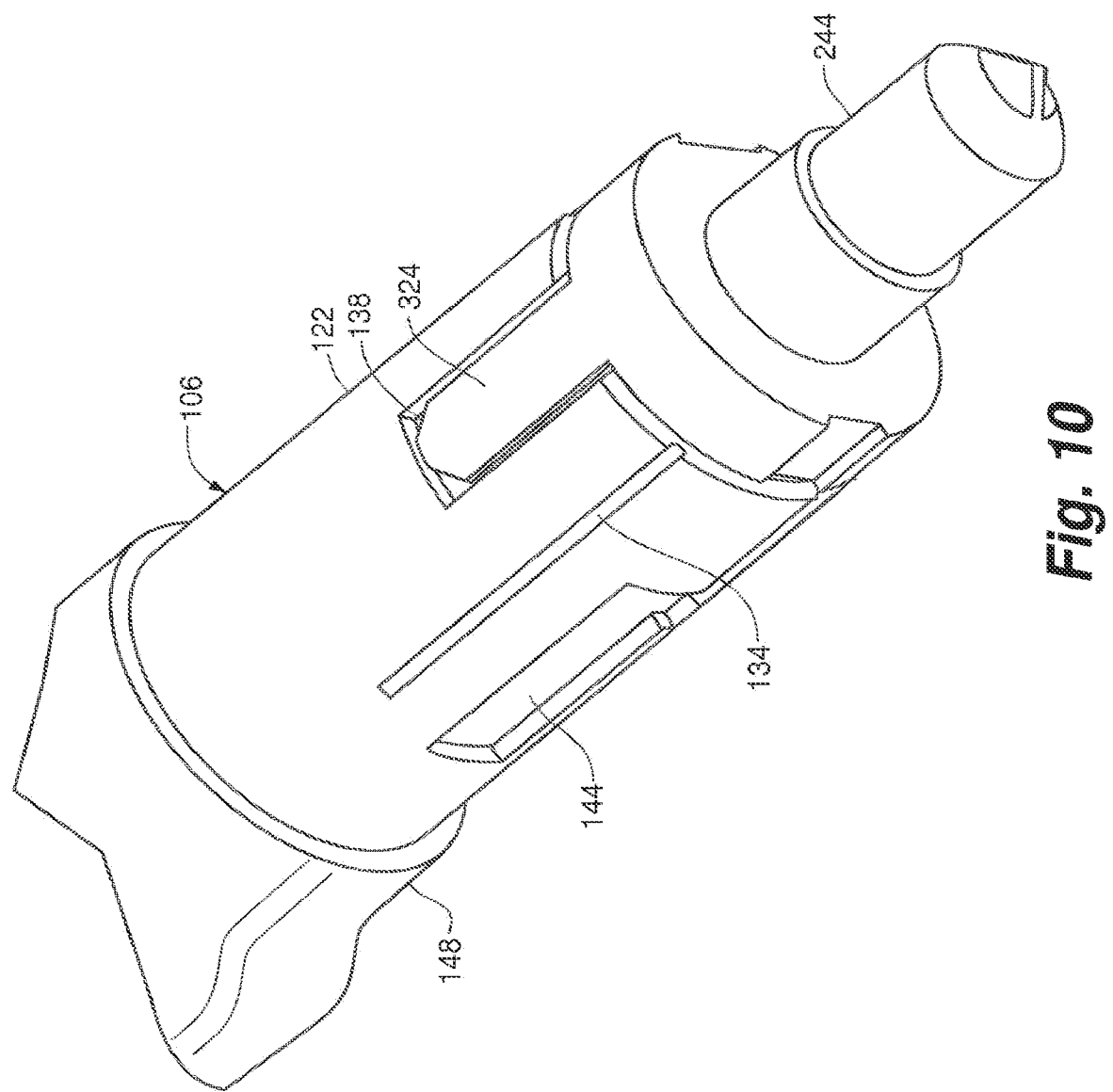
FIG. 10 is a perspective view of the body and plunger of FIGS. 7 and 9, the plunger having been guided axially toward the body, according to an embodiment.
Figure 11:
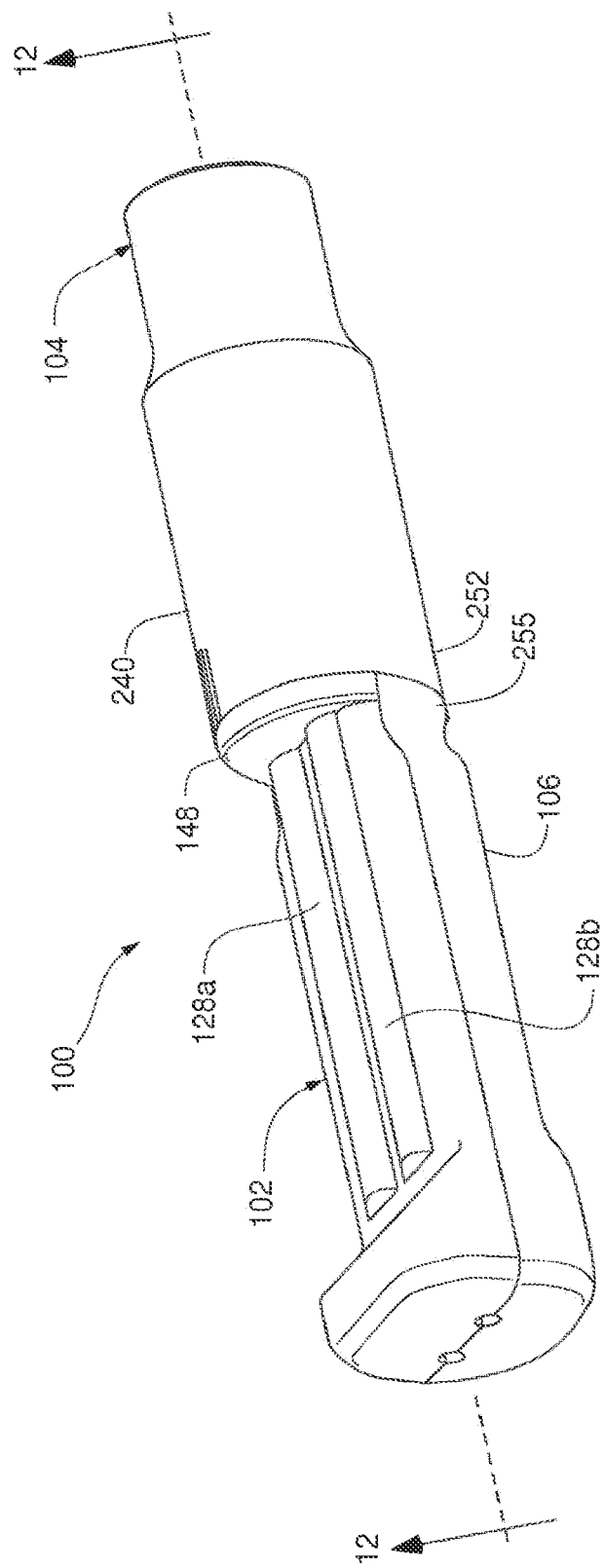
FIG. 11 is a perspective view of the testing device of FIG. 1 in a final engagement position, according to an embodiment.

Referring also to FIGS. 10 and 11, cap-engagement portion 122 may also include one or more plunger-guide channels 138. In an embodiment, plunger-guide channel 138 extends axially from first end 124 towards second end 132, and defines a linear channel, groove, slot, or slit. As depicted, plunger-guide channel 138 does not penetrate a wall of body portion 106, but in other embodiments, may penetrate body portion 106 to define a slot or opening to an interior space of body portion 106.

Cap-engagement portion 122 may also include annular ring 148 where cap-engagement portion transitions to viewing-window portion 126. Annular ring 148 may define an outer diameter greater than an outer diameter of first end 124, including surface 150, thereby functioning as a stop for cap assembly 104.

In an embodiment, viewing-window portion 126, in addition to viewing windows 128a and 128b, includes view-window surface 152 and defines recess 154. Viewing windows 128a and 128b as depicted comprise semi-cylindrical portions extending axially along surface 152 and located within associated openings in first body portion 114. In an embodiment, surface 152 presents a generally flat, planar surface 152. In an embodiment, and as depicted, body assembly 102 includes two viewing windows 128, one for each test strip 108. However, in other embodiments, only one window 128 may be present so as to view one or more test strips 108, or more than two windows 128 may be present to view multiple test strips 108.

Viewing windows 128a and 128b may comprise a transparent or translucent material that allows a user to see into body portion 106 and view test strips 108. As depicted, viewing windows 128a and 128b are curved, and in some cases may provide a magnifying effect so as to aid in the viewing of test trips 108. In other embodiments, viewing windows 128 may comprise flat or planar portions that may be coplanar with surface 152.

In an embodiment, viewing-window portion 126 defines a circumference that may easily be grasped by a user's hand, a portion of which may be received by recess 154, which is bounded by view portion 130 and ring 150.

Vent portion 130, in an embodiment, includes beveled surface 156, top surface 158 and end surface 160 of end wall 162, and radial wall 164. Vent portion 130 defines one or more vent holes 166 in end wall 162. As depicted, vent portion 130 includes two outer vent holes 166a and 166b.

Figure 3:
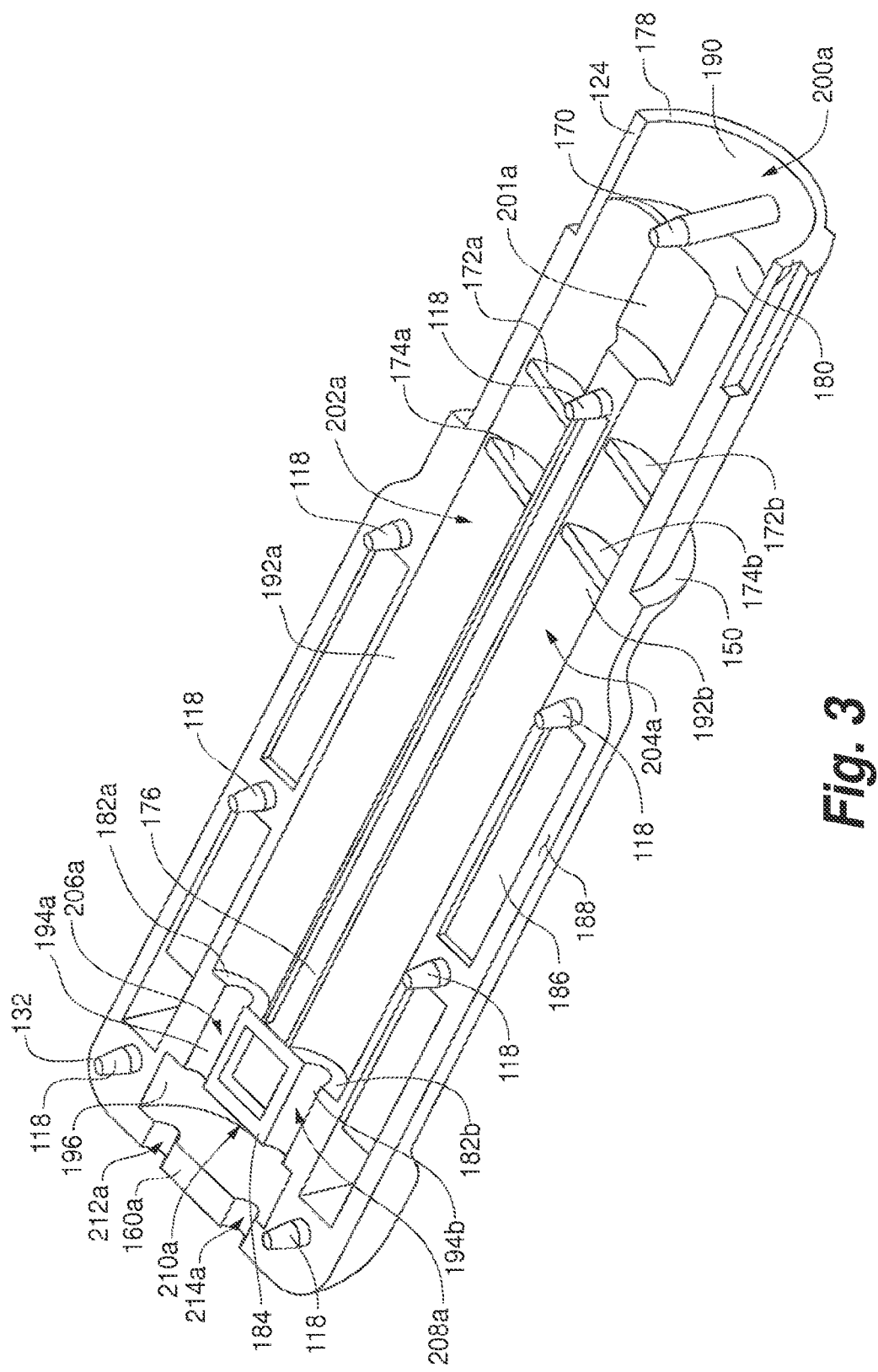
FIG. 3 is a bottom perspective view of a first body portion of a body assembly of the testing device of FIG. 1, according to an embodiment.
Figure 4:
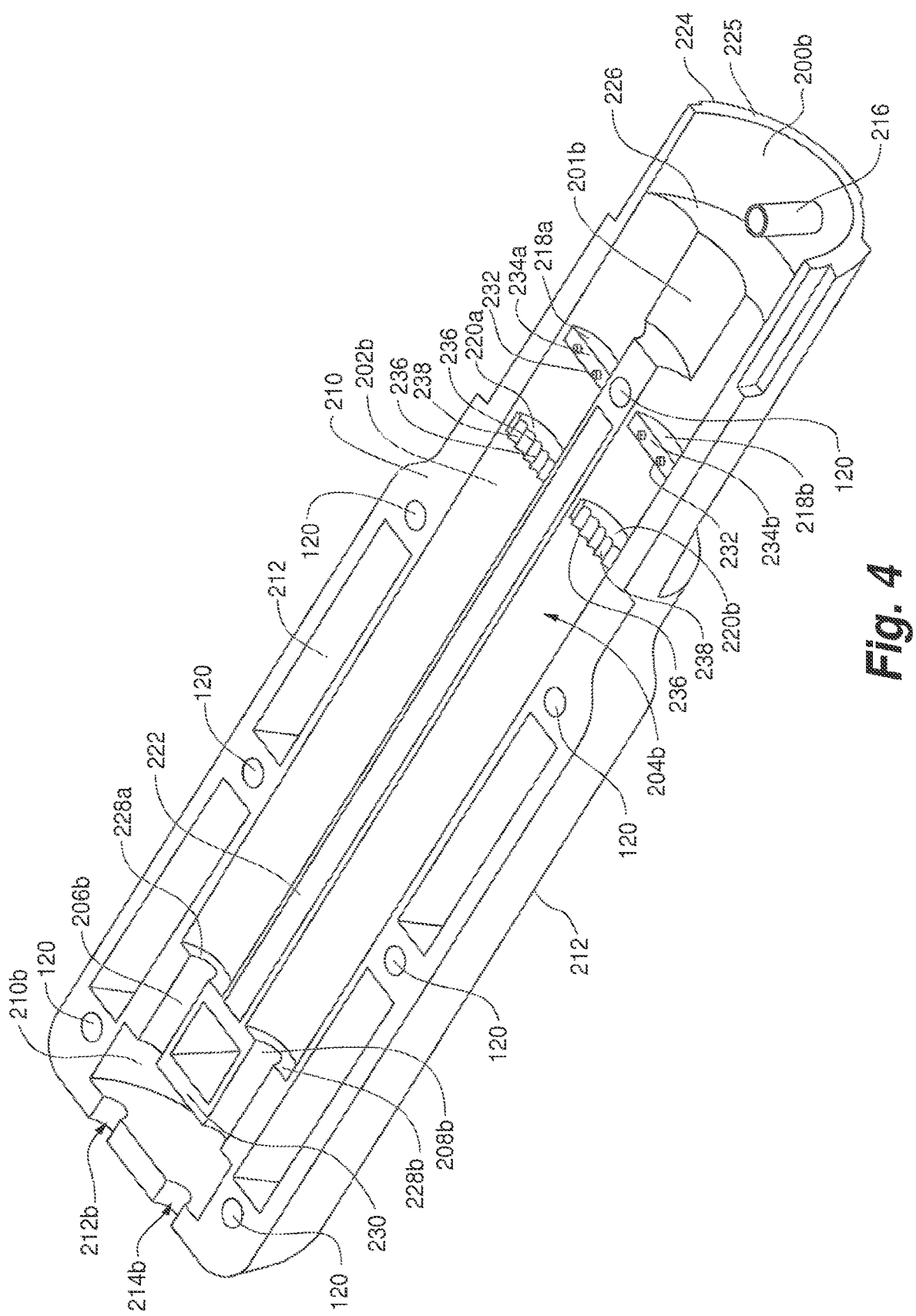
FIG. 4 is a top perspective view of a second body portion of a body assembly of the testing device of FIG. 1, according to an embodiment.

Referring to FIGS. 3 and 4, top perspective views of first body portion 114, and second body portion 116, are respectively depicted. As described further below, each body portion presents a contoured inner surface defining a plurality of channels and recesses. Further, in an embodiment, the inner surfaces of each body portion are substantially the same, with the exception of a few features, including pins 118 versus holes 120. When assembled together to form body portion 106, each body portion 114 or 116 defines one half of a channel or recess of body portion 106.

Referring specifically to FIG. 3, first body portion 114 includes sponge pin 170, first proximal bridges or dividers 172a and 172b, first distal bridges or dividers 174a and 174b, first central wall 176, first outer wall 178, first collection sponge wall 180, first vent walls 182a and 182b, first vent sponge wall 184, and presents inner contoured surface 186.

Inner contoured surface 186 includes a number of surfaces, including flat first edge surface 188 extending about a periphery of first body portion 114, curved first collection sponge surface 190, curved first test strip channel surfaces 192a and 192b, curved first inner vent hole surfaces 194a and 194b, and curved first vent sponge surface 196.

Inner contoured surface 186 and its surfaces above define a number of cavities and channels, including first collection sponge cavity 200a, first fluid reservoir 201a, first test strip channel 202a, second test strip channel 204a, first inner vent channel 206a, second inner vent channel 208a, first vent sponge cavity 210a, first outer vent channel 212a, and second outer vent channel 214a.

First collection sponge cavity 200a is located at first end 124, is defined by outer wall 178, first collection sponge wall 180 and surface 190, and in an embodiment is shaped to receive a portion of cylindrically-shaped collection sponge 112.

Each of first and second test strip channels 202a and 204a extend axially along inner contoured surface 186, defined by surfaces 192a, 192b, and walls 182a, 182b, respectively. Channels 202a and 204a define generally semi-cylindrical channels. Bridges 172a and 174a each span a width of first test strip channel 202a, dividing the channel into three portions. Bridges 172b and 174 similarly span a width of second test strip channel 202b, dividing the channel into three portions.

Inner vent channels 206a and 206b are defined by curved surfaces 194a and 194b, respectively, also extending axially.

First vent sponge cavity 210a is configured to receive a portion of disc-shaped vent sponge 110, such that it has a semi-circular shape when viewed in cross section. Cavity 210a is defined by wall and surface 196.

Referring to FIG. 4, second body portion 116 is depicted. As described above, second body portion 116 includes structure substantially the same as first body portion 114. As such, second body portion 116 includes inner contoured surface 210 having multiple individual surfaces defining multiple cavities and channels. Contoured surface 201 defines second collection sponge cavity 200b, second fluid reservoir 201b, first test strip channel 202b, second test strip channel 204b, inner vent channels 206b and 208b, second vent sponge cavity 210b, and outer vent channels 212b and 214b. In some embodiments, second body portion 116 may also define one or more material-saving voids 212, which may be implemented via an injection-molding process.

Each cavity and channel of second body portion 116 includes a counterpart cavity and channel of first body portion 114, such that when first body portion 114 is coupled to second body portion 116 causing contoured surface 186 to contact contoured surface 210, each of the respective cavities and channels form a cavity and channel of body portion 106. In other words, first and second collection sponge cavities 200a and 200b combine to form collection sponge cavity 200 of body portion 106; first and second fluid reservoirs 201a and 201b form fluid reservoir 201; first test strip channels 202a and 202b form first test strip channel 202; second test strip channels 204a and 204b form second test strip channel 204; inner vent channels 206a and 206b form inner vent channel 206; inner vent channels 208a and 208b form inner vent channel 208, first and second vent sponge cavities 210a and 210b form sponge cavity 210; outer vent channels 212a and 212b form outer vent channel 212; outer vent channels 214a and 214b form outer vent channel 214. Outer vent channel 212 also defines outer vent hole 166a, while outer vent channel 214 also defines outer vent hold 166b (see also FIG. 1).

In an embodiment, second body portion 116 also includes additional structural features, including sponge-pin receiver 216, second proximal bridges or dividers 218a and 218b, second distal bridges or dividers 220a and 220b, second central portion 222 (which in an embodiment may define a central channel receiving a portion of first central wall 176), second outer wall 224 forming rim 225, second collection sponge wall 226, second vent walls 228a and 228b, and second vent sponge wall 230.

In an embodiment, and as depicted, second proximal bridges 220a and 220b may include one or more projections 232 projecting radially away from top surfaces 234a and 234b. Second proximal bridges 220a and 220b may include similar projections. In an embodiment, and as depicted each bridge 220 includes two projections 232, although fewer or more projections may be present.

In an embodiment, and as depicted, second distal bridges 220a and 220b include ridges 236 and define grooves 238.

Referring again to FIGS. 1 and 2, in an embodiment, cap assembly 102 includes cap 240, fluid container 242, and plunger 244. When assembled, and as discussed further below, fluid container 242 and plunger 244 are housed within cap 240.

Figure 5:
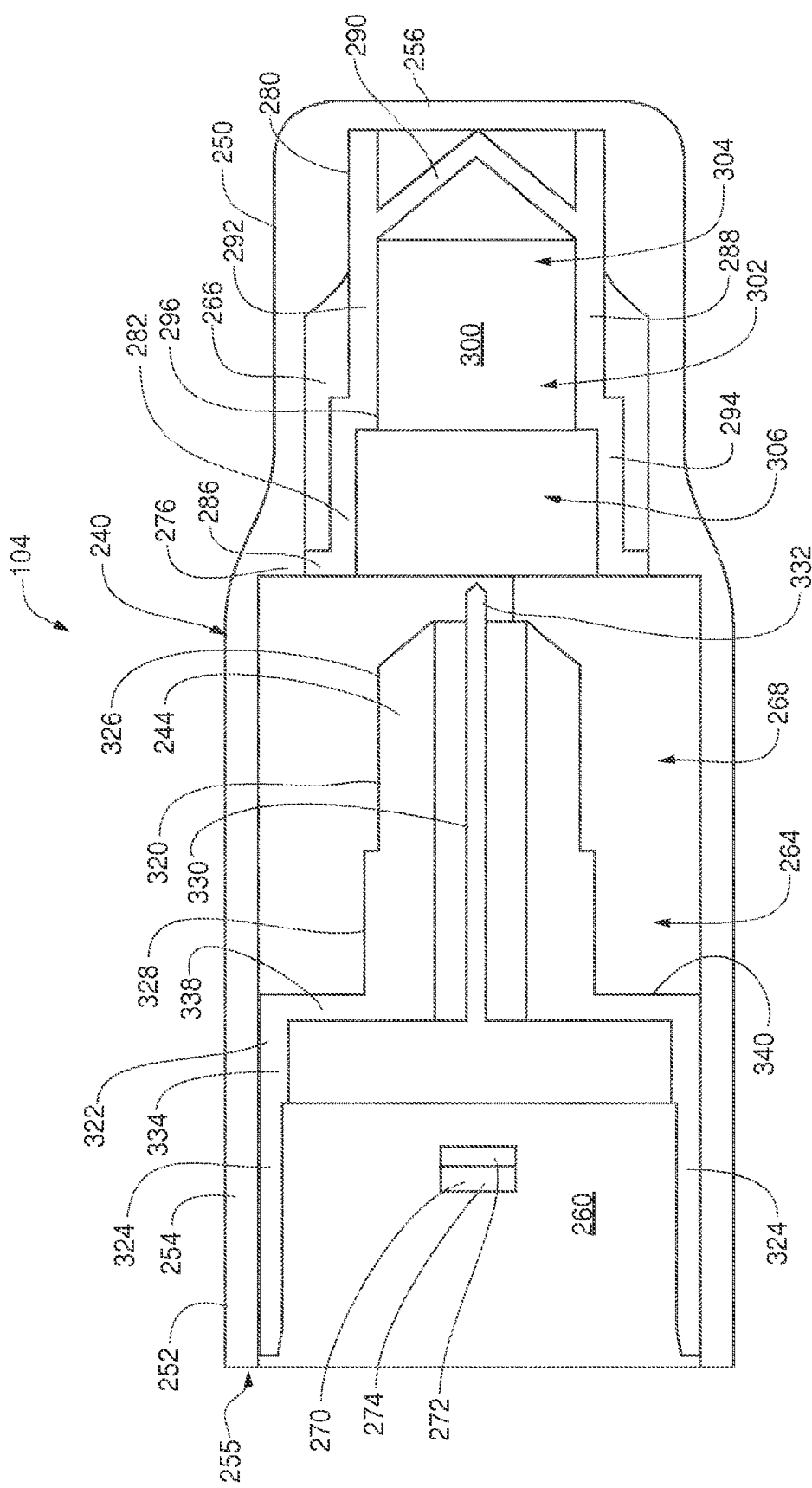
FIG. 5 is a cross-sectional view of a cap assembly of the testing device of FIG. 1, in an initial alignment position, according to an embodiment.

Referring also to FIG. 5, cap 240, in an embodiment, comprises a polymer material defines a generally cylindrical or tubular shape. Cap 240 includes first end 250, second end 252, circumferential wall 254 with edge 255, and end wall 256. Cap 240 also defines outside surface 258 and inside surface 260. In an embodiment, second end 252 also includes one or more body-cap visual alignment indicators 262. As depicted, second end 252 includes two alignment indicators 262, each comprising a ridge extending axially along outer surface 258, and opposite one another. Second end 252 defines an opening into cap cavity 264, a hollow portion of cap 240 defined by wall 254 and into which fluid container 242 and plunder 244 are inserted. In an embodiment, cap cavity 264 defines first cavity portion 266 and second cavity portion 268.

In an embodiment, cap 240 also includes one or more alignment members 270 comprising protuberances projecting radially inward from inside surface 260 (FIG. 5). In an embodiment, cap 240 includes two alignment members 270, each member 270 opposite the other within cap 240. In an embodiment, alignment members 270 each include a beveled edge 272 and a top surface 274.

Cap 240 may also include shoulder 276 at the transition between first cavity portion 266 and second cavity portion 268. In an embodiment, shoulder 276 forms an annular ring within cap 240, and as will be described further below, serves as a stop for plunger 242.

In an embodiment, first end 250 may define a diameter that is slightly smaller than a diameter of second end 252, thereby conforming to end 124 of body assembly 102.

Referring still to FIGS. 2 and 5, in an embodiment, fluid container 242 includes closed first end 280, open second end 282, body portion 284, and flange 286. In an embodiment, body portion 284 comprises outer circumferential wall 288 forming body portion 284, end wall 290 forming closed first end 280, first body portion 292, second body portion 294, and shoulder 296. Shoulder 296 is adjacent first body portion 292 and second body portion 294, at the transition between the two portions. Fluid container 242 presents outside surface 298 and inside surface 300.

Fluid container 242 defines inside cavity 302, which defines first cavity portion 304 and second cavity portion 306, formed by first body portion 292 and second body portion 294, respectively.

Figure 8:
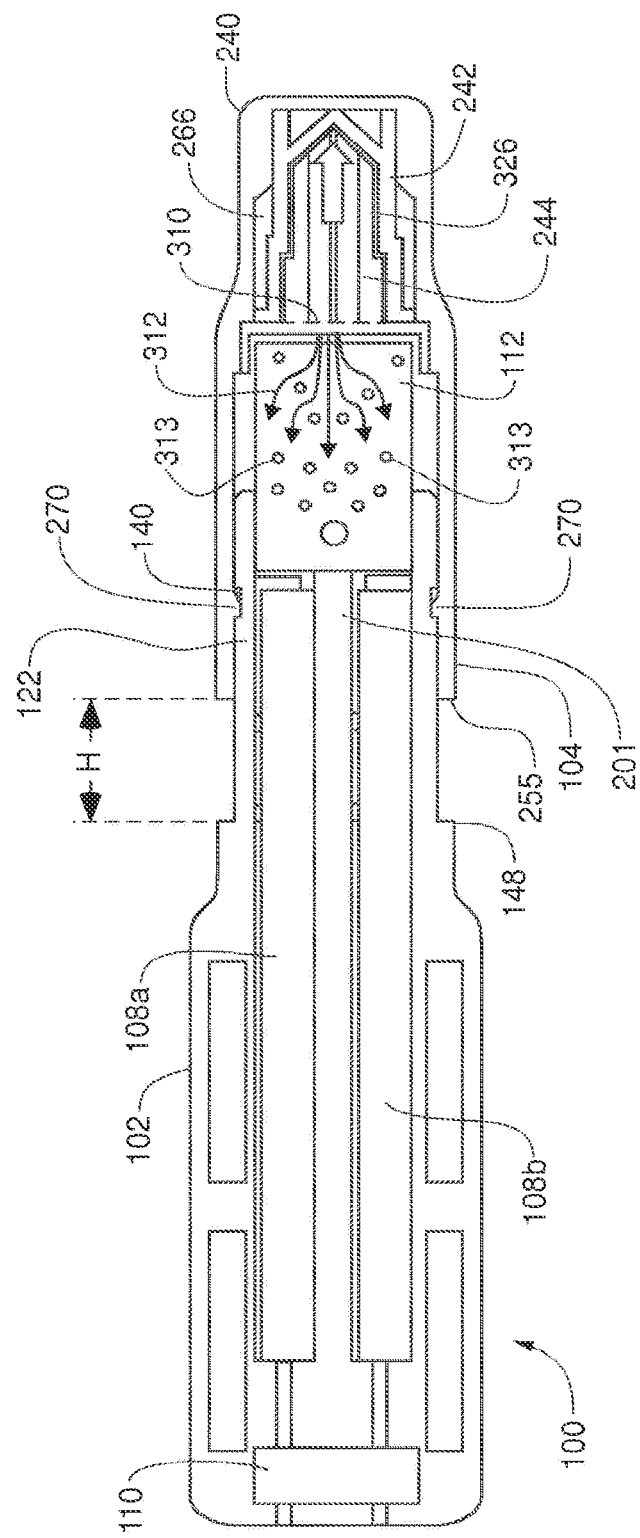
FIG. 8 is a cross-sectional view of the testing device of FIG. 1 depicting a first-stage fluid flow path, according to an embodiment.

Fluid container 242 also includes barrier or membrane 310 and fluid 312 (see FIG. 8). Initially, fluid 312 is contained within fluid container 242. Fluid 312 in an embodiment comprises a buffer solution intended to be mixed with oral fluid, such as saliva, collected by testing device 100. Membrane 310 extends across an opening of cavity 302 and to flange 286, thereby keeping fluid 312 within fluid container 242. In an embodiment, membrane 310 may comprise a foil membrane or barrier, but may alternately comprise some other penetrable material, such as a plastic or polymer.

In an embodiment, fluid container 242, as depicted may form a generally cylindrical shape. Fluid container 242 is generally shaped and configured to conform with, and fit into, first cavity portion 266 of cap 240. In other embodiments fluid container 242 may comprise other shapes configured to fit into cap 300.

Plunger 244, in an embodiment, and as depicted, includes body portion 320, cup portion 322, and extensions 324.

In an embodiment, body portion 320 includes first end 326, second end 328, and defines fluid channel 330. First end 326 includes penetrating tip 332 for penetrating membrane or barrier 310. Second end 328 is adjacent cup portion 322. Fluid channel 330 extends axially from tip 332 through body portion 320, opening into cup 322. In an embodiment, fluid channel 330 also extends into and through tip 332.

In an embodiment, body portion 320 is configured and shaped to conform to, or fit into, cavity 302 of fluid container 242.

Cup portion 322, adjacent body portion 320, in an embodiment, includes ring portion 334 with outer ring surface 336, and end wall 338 with end surface 340. Ring portion 334 may generally comprise a ring or disc shape; end wall 338 in an embodiment comprises a generally flat, planar surface. Together, ring portion 334 and end wall 338 form cup cavity 342, which, in an embodiment, is configured to receive a portion of collection sponge 112. Cup portion 322 also presents inner surface 344 comprising an inner surface of ring portion 334 and an inner surface of end wall 338.

In an embodiment, and as depicted, plunger 244 includes two extensions 324, opposite one another, and affixed to ring portion 344. However, in other embodiments, plunger 244 may include one, or more than two, extensions 324. In an embodiment, each extension 324 comprises a generally flat, strip-like portion extending axially away from an edge of ring portion 334. In other embodiments, extensions 324 may comprise other structures, such as columns, and so on, extending axially away from ring portion 334.

Referring specifically to FIG. 5, cap assembly 104 is depicted in an initial, or shipping, configuration, with fluid container 242 received in first cavity 266 of cap 240, and plunger 244 received in second cavity 268. In an embodiment, plunger 244 is not engaged, or is only minimally engaged, with fluid container 242. In other embodiments, fluid container 242 may be integrated with plunger 244.

As depicted, plunger 244 is slidably engaged with cap 240, such that outer ring surface 336 of plunger 244 is in contact with inner surface 260 of cap 240.

Referring again to FIGS. 1 and 2, body assembly 102 includes one or more test strips 108. As depicted, body assembly 102 includes two test strips, 108a and 108b. In an embodiment, each test strip 108 comprises a generally flat, planar strip including a first end 350 (350a, 350b) and second end 352 (352a, 352b), and presenting a top surface 354 (354a, 35b) and bottom surface 356 (356a, 356b).

As will be understood by those of ordinary skill in the art, test strips 108 may comprise an immunoassay strip adapted to indicate the absence or presence of specific chemicals, typically pharmaceuticals or drugs. Test strips 108 typically indicate the presence of a chemical by changing color, the color being visible to a user.

In an embodiment, body assembly 102 includes vent sponge 110. In an embodiment, and as depicted, vent sponge 110 comprises an absorbent sponge material forming a disc shape.

Body assembly 102 also includes oral-fluid collection sponge 112 comprising an absorbent sponge material and forming a generally cylindrical shape. In other embodiments, collection sponge 112 may comprise a disc-like shape, or other shape. Collection sponge 112 includes first end 360, second end 362, and in an embodiment, defines channel 364. First end 360 of sponge 112 is received by body portion 106, with pin 170 and pin receiver 216 being received by channel 364 to position and secure collection sponge 112 relative to body 106. Second end 362 extends axially and away from body 106, and includes end surface 366. Other structural embodiments may be utilized for retaining the sponge, such as adhesives, barbs, clamp structure for compressing and securing a flange.

Figure 6:
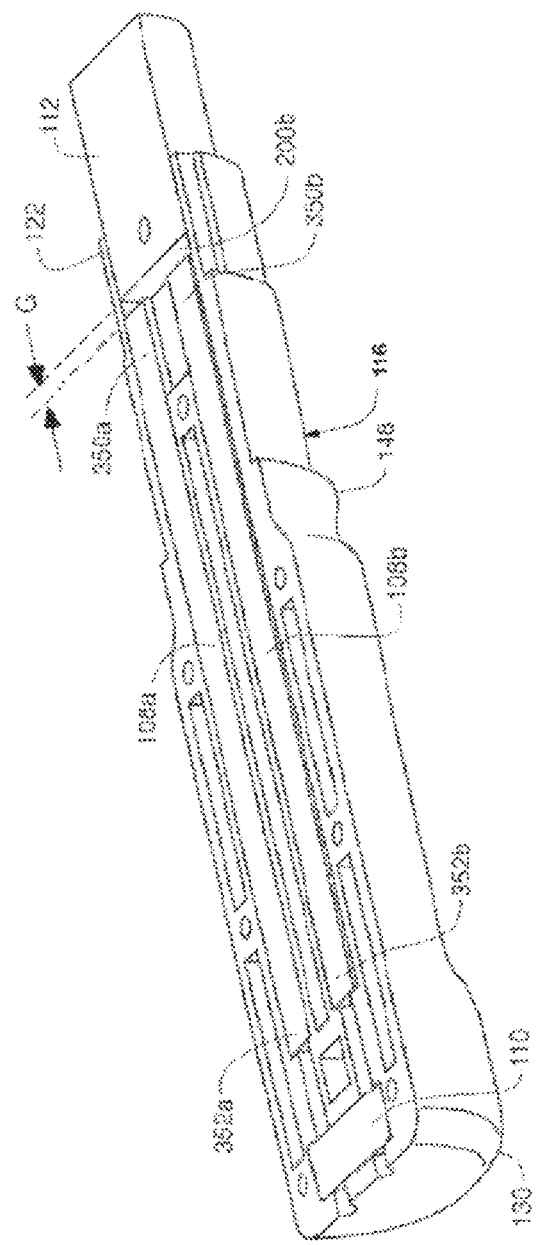
FIG. 6 is a perspective view of the second body portion of FIG. 4 with sponges and test strips.

Referring to FIG. 6, second body portion 116 with test strips 108a, 108b, vent sponge 110 and collection sponge 112, is depicted. Referring also to FIG. 4, test strips 108a and 108b are fit into test strip channels 202b and 204b, respectively. First ends 350a,b are adjacent sponge cavity 200b, while second ends 352a,b, are in or adjacent to vent portion 130 of body 106. First ends 350a,b are adjacent to, and in contact with bridges 218a, b, and 220a, b. More specifically, projections 232 and ridges 236 contact bottom surfaces 356a,b of test strips 108a,b. In some embodiments, test strips 108 may be compliant enough that portions of bottom surfaces 356a,b also contact top surfaces 234 and grooves 238. When first body portion 114 is coupled to second body portion 116, test strips 108 may be compressed somewhat by bridges 218 and 220, thereby maintaining an axial position of each test strip 108 relative to body 106.

Vent sponge 110 is received by vent sponge cavity 210.

Collection sponge 112 is received by collection sponge cavity 200, and as described above, positioned and secured by pin 170 and pin receiver 216 (see also FIG. 5). In an embodiment, and as depicted, a gap G exists between sponge 112 and first ends 350 of test strips 108, such that sponge 112 is not in direct contact with test strips 108. In such an embodiment, and as will be described further below, a more uniform capillary effect may be achieved by avoiding such direct contact. In other embodiments test strips 108 may directly contact collection sponge 112.

Referring generally to FIGS. 7-14, collecting and testing an oral fluid using oral-fluid collecting and testing device 100 is depicted.

Referring to FIGS. 1 and 5, testing device 100 may be shipped, and/or received by a user as a two-piece item, namely body assembly 102 and cap assembly 104. A sample of an oral fluid, such as saliva is received by first end portion 362 of collection sponge 112. Collection sponge 112 may be swabbed inside the mouth of a person or animal whose fluid is to be tested, such a person may spit onto, or otherwise supply the oral fluid onto sponge 112.

After oral fluid is received or and absorbed by collection sponge 112, cap assembly 102 may be aligned axially along axis A with body assembly 102 as depicted in FIG. 1. Cap assembly 104 and body assembly 102 may then be axially moved towards one another. Alignment indicators 262 may be aligned with visual-alignment grooves 134 so as to rotationally align cap assembly 104 with body assembly 102, thereby positioning cap assembly 104 at body assembly 102 in preparation for body assembly 102 receiving cap assembly 104.

Figure 7:
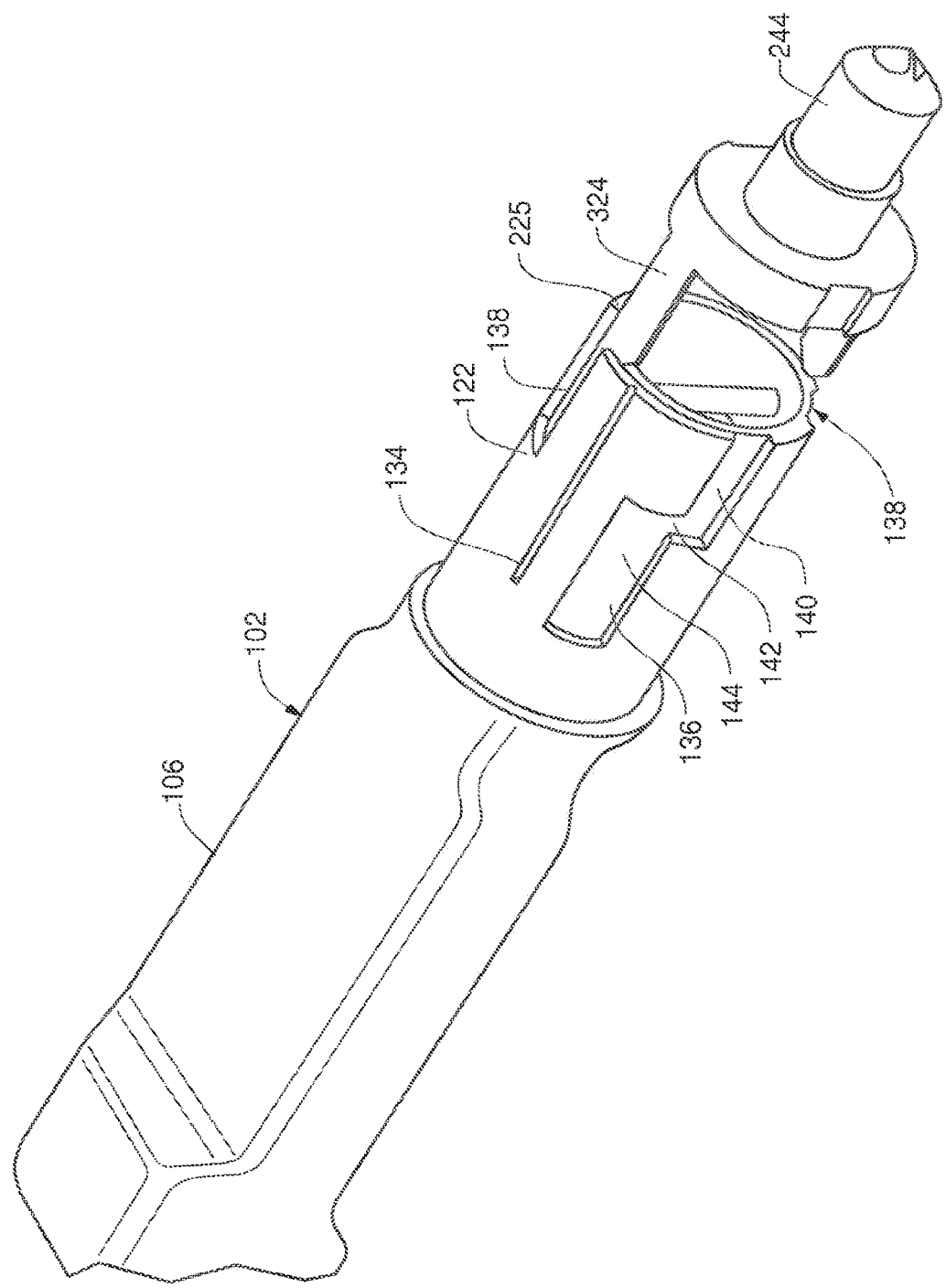
FIG. 7 is a perspective view of a body and plunger of the testing device of FIG. 1, the plunger aligned with the body in an initial alignment position, according to an embodiment.

Referring to FIG. 7, body assembly 102, without collection sponge 112 and plunger 244 are depicted in an initial position. Alignment of visual indicators 262 (FIG. 1) with grooves 134 results in the depicted rotational orientation of plunger 244 relative to cap engagement portion 122. In this initial position, an end of each of extensions 324 of plunger 244 are adjacent, and in some embodiments, in contact with, rim or edge 225. Rim 225, in an embodiment, may include a beveled edge.

In this initial engagement position, in an embodiment, extensions 324 are not yet aligned with plunger-guide channels 138, such that even if an axial force is applied to plunger 244, extensions 324 merely contact rim 225, and are generally unable to move axially relative to body 106. As described further below, plunger 244 must be rotated so as to align channels 138 with extensions 324 before plunger 244 may be moved axially onto cap-engagement portion 122 of body 106.

Referring to FIG. 8, cap assembly 104 is depicted in a second position relative to body assembly 103. In this second engagement position, cap assembly 104 has moved axially relative to body assembly 102, and has received a portion of cap-engagement portion 122. Alignment members 270 are received by first channel portions 140 of cap-guide channels 136 (see also FIG. 7), having "traveled" along channel portion 140. Fluid container 242 remains seated in first cavity 266 of cap 250. A gap H remains between cap edge 255 of cap 240 and ring 148, which serves as a stop for cap 240.

Cap assembly 104 is prevented from being moved further in an axial direction not only due to the contact of extensions 324 with body 106, but also because, in an embodiment, alignment members 270 have traveled the entire length of axial channel 140, arriving at radial channel 142 (see also FIG. 7). Until cap assembly 102 is rotated into another alignment position, cap assembly 102 cannot move further axially onto body 106.

A portion of plunger 244 is received by fluid container 242. More specifically, tip 332 (see FIG. 5 also), after penetrating membrane 310, has traveled along with first end 326 into cavity 302 of fluid container 242, so as to be in the depicted position. The arrow indicates a direction of movement of plunger 242 relative to fluid container 242.

Fluid 312 flows from fluid container 242 into and through plunger fluid channel 330, out of plunger 244, and onto collection sponge 112, as indicated by the multiple smaller arrows, and as caused by the movement of cap assembly 104 onto body assembly 102. Fluid 312 from fluid container 242 is absorbed by collection sponge 112 and mixes with oral fluid already absorbed by collection sponge 112 to form oral-fluid mixture 313.

Simultaneously, air that may have become trapped between cap assembly 104 and body assembly 102 is expelled from body assembly 102. More specifically, an exhaust air flow path is formed by the combination of collection sponge 112 with sponge cavity 200, fluid reservoir 201, test strips 108 with test strip channels 204, inner exhaust channels 206, vent sponge 110 with sponge cavity 210, and outer exhaust channels 212. Vent sponge 110 functions to trap and absorb any stray fluid that should migrate all the way to vent portion 130, so as to prevent any unwanted release of fluid from testing device 100.

In this second engagement position, collection sponge 112 is not yet compressed by plunger 244, such that oral-fluid mixture 313 is generally contained on and within collection sponge 112, rather than at test strips 108.

The above release of fluid 312 onto oral-fluid soaked collection sponge 112, and simultaneous air exhaustion, describes another stage of the multi-stage collection and test procedure. As described above, in an embodiment, collection of oral fluid may comprises a first stage or step. Another stage or step may include the alignment of cap assembly 104 with body assembly 102.

At the next stage or step, cap assembly 104 and its plunger 244 are rotated relative to body assembly 102, such that cap assembly 104 with plunger 244 may be moved further in an axial direction along cap-engagement portion 122.

In an embodiment, a user waits a period of time, which may be predetermined, before proceeding with the rotation step so as to allow time for fluid 312 to be fully absorbed into sponge 112 and to mix with the oral fluid to form oral-fluid mixture 313.

Referring to FIG. 9, plunger 244 is depicted after being rotated relative to body 106. Referring also to FIG. 7, in an embodiment, cap assembly 104 and plunger 244 are depicted as being rotated approximately 22 degrees in a clockwise direction. In other embodiments, the degree of rotation may vary. In one such embodiment, plunger 244 is rotated approximately 44 degrees. In another embodiment, plunge 244 may be rotated from 20 degrees to 50 degrees; in another embodiment plunger 244 may be rotated from 10 to 90 degrees. Other embodiments may allow for other rotational ranges.

In this rotated position, extensions 324 are axially aligned with plunger-guide channels 138. Although not depicted, it will be understood that during rotation, alignment members 170 travel radially within radial channels 142 to become aligned with axial channels 144 (see also FIGS. 7 and 8). In this position, cap assembly 104 is capable of travelling further in an axial direction toward ring 148 when an axial force is applied to cap assembly 104. Further, plunger 144 will travel simultaneously with cap 240 as cap assembly 104 travels axially.

Referring to FIG. 10, after such an axial force is applied, plunger 244, guided by extensions 324 traveling in plunger-guide channels 138 seats on cap-engagement portion 122 of body 106 as depicted.

Referring also to FIG. 11, cap assembly 104 engaged with body assembly 102 in a final engagement position is depicted in a perspective view. In this position, second end 252 and edge 255 of cap 240 are seated against ring 148. Plunger 244 is engaged with body 106 as depicted in FIG. 10. Some trapped air has been exhausted out of body assembly 102, and as depicted and described below, collection sponge 112 is compressed, causing oral-fluid mixture 313 to flow into fluid reservoir 201, and be absorbed by test strips 108.

Figure 12:
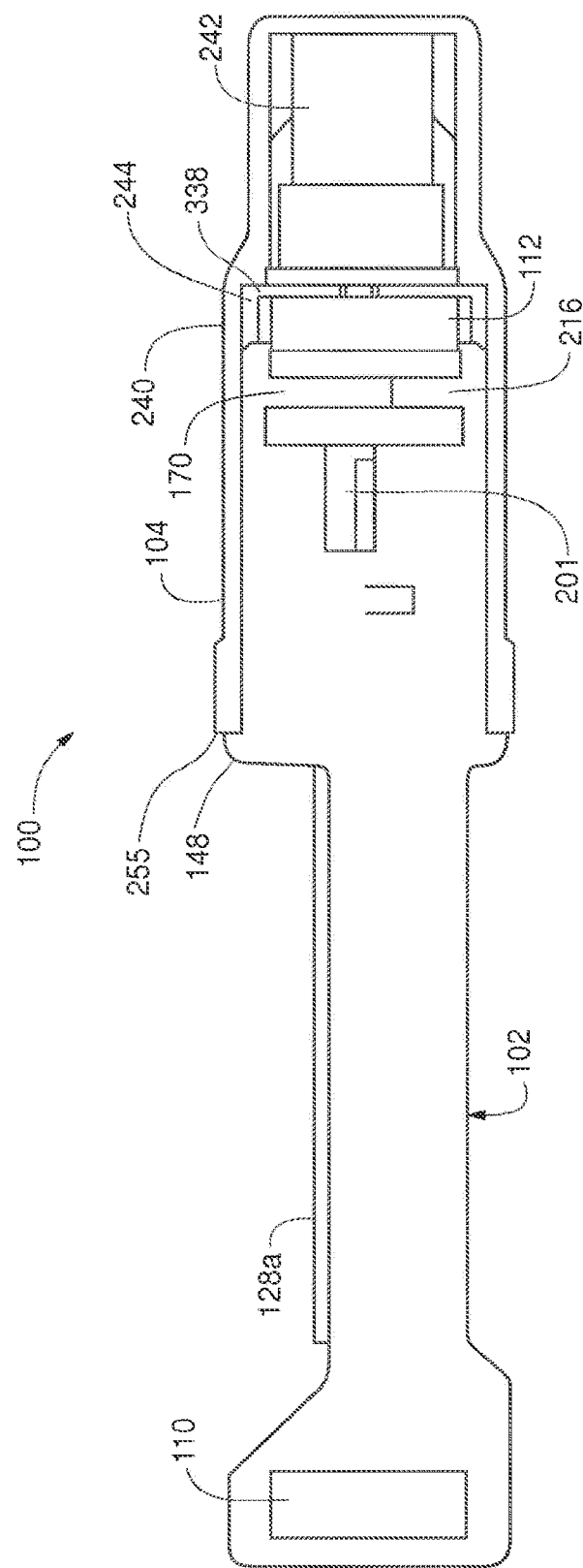
FIG. 12 is a cross-sectional view of the testing device in the final engagement position as depicted in FIG. 11.

Referring to FIG. 12, cap assembly 104 engaged with body assembly 102 in a final engagement position is depicted in cross section (fluid container 242 is not depicted in a cross-sectional view). In this final position, cup portion 322 at end wall 338 engages collection sponge 112 in a compressed position. The compression of collection sponge 112 causes oral-fluid mixture 313 to flow from sponge 112 and into fluid reservoir 201, as depicted in FIG. 13.

In an embodiment, cap-engagement portion 122 of body 106 may include a snap ring to engage inside surface 260 of cap 240 to hold cap assembly 104 in a final engagement position. This may be a locked position such that the cap assembly is not readily removable without tools. Attempt to remove same will be at least difficult and may, in particular embodiments, requiring breaking the device if specialized tools are not used.

Figure 13:
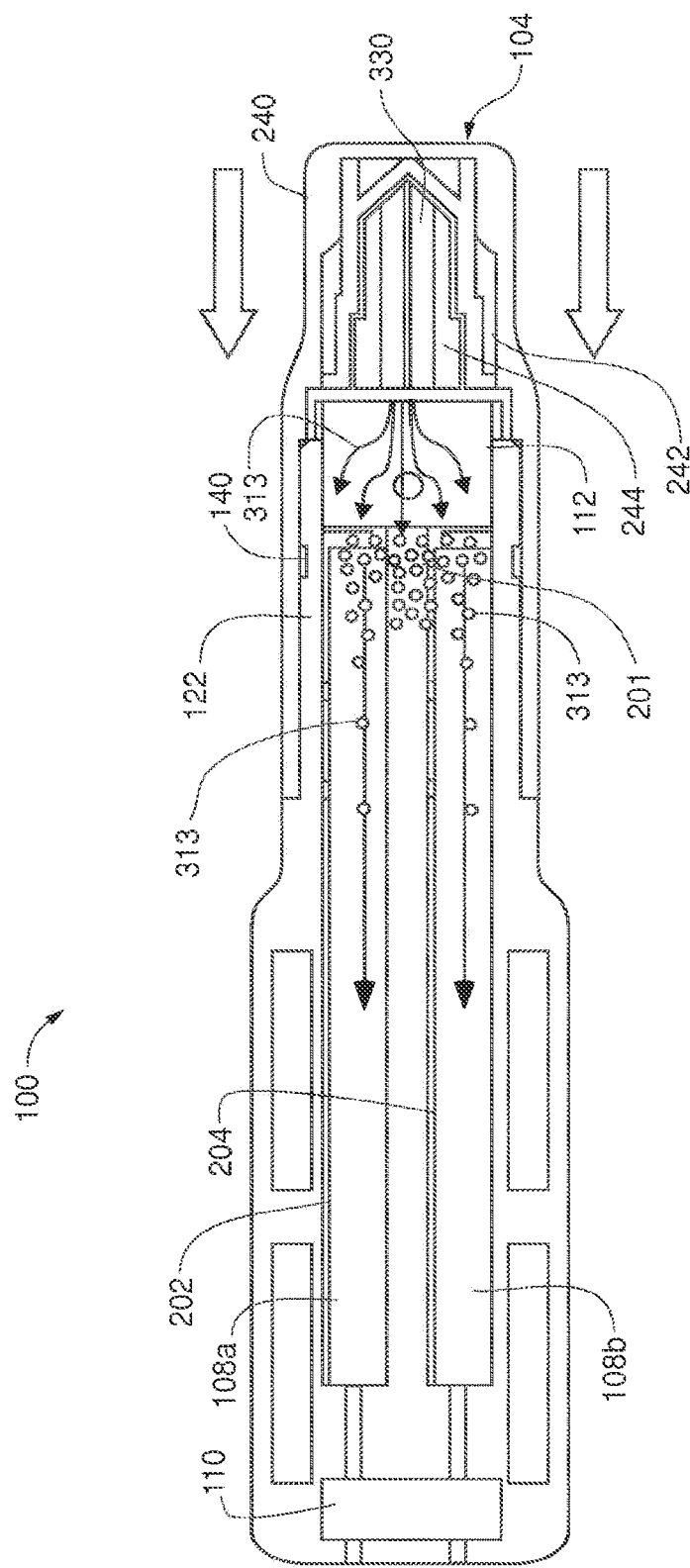
FIG. 13 is a cross-sectional view of the testing device of FIG. 1 in a final engagement position, and depicting a second-stage flow path.

Referring to FIG. 13, a flow diagram of oral-fluid mixture 313 is depicted in testing device 100. As discussed above with respect to FIG. 12, collection sponge 112 is compressed due to the axial translation of cap 240 in a direction indicated by the arrows, causing oral-fluid mixture 313 to exit sponge 112 in a generally axial direction into reservoir 201 and toward test strips 108. As fluid reservoir 201 fills, oral-fluid mixture 313 comes into contact with test strips 108. Oral-fluid mixture is drawn through channels 202 and 204 and test strips 108 in a generally axial direction from reservoir 201 toward distal end 132, as indicated by the arrows on test strips 108. Flow of oral-fluid mixture 313 is aided by wicking and capillary effects. Capillary rise may be improved with the compression of test strips 108 by bridges 172, 174, 218 and 220 (see also FIGS. 4 and 5). Further bridges 172, 174, 218 and 220 also prevent incidental splashing of oral-fluid mixture 313 onto viewing windows 126 or in the general vicinity thereof.

As oral-fluid mixture 313 travels or migrates along test strips 108, an appropriate chemical reaction occurs, indicating the presence (or absence) of a particular chemical in oral-fluid mixture 313. As described briefly above, and as will be understood, the presence of a tested-for chemical is typically indicated by a display or change of color.

In an embodiment, first test strip 108a tests for a first substance, and second test strip 108b tests for a second substance. In one such embodiment, first and second substances comprise different substances. In another embodiment, first and second substances comprise the same substance.

As portions of test strips 108 are generally visible through viewing windows 126, when strips 108 present a color or other indication, such an indication will be visible to a user looking at viewing windows 126, such that the absence or presence of the tested-for chemical or substance in the oral fluid of a donor is indicated to the user.

In accordance with the above description, in an embodiment, methods of the claimed invention include a method for testing for a substance using a testing device that includes a cap assembly 104 having a plunger 244 and a fluid container 242 with a reservoir, as well as a body assembly 102 that includes a body portion with test strips 108 and a collection sponge 112, the method including collecting an oral-fluid sample onto the collection sponge 112, rotationally aligning the cap assembly 104 with the body assembly 102 by aligning visual indicators 162, 134 on both the cap assembly and body assembly, applying a first axial force to the cap assembly 102 causing it to move axially toward the body assembly 102, thereby causing the plunger 244 to penetrate a membrane of the fluid container 242 such that in a first-stage fluid flow process, a fluid 312 in the fluid container 242 flows to the sponge 112 which is in an uncompressed state.

In an embodiment, the above method also includes waiting for a predetermined period of time, then rotating the cap assembly 104 to align extension portions 324 of the plunger to align with plunger guide channels 138, followed by applying a second axial force to the cap assembly 104 causing the plunger 244 and cap 240 to move axially further toward a distal end of the body assembly 102 and causing the collection sponge 112 to be compressed such that it releases its oral-fluid mixture 313 into a reservoir 201 of the body assembly 102, and to contact a test strip 108.

In a further embodiment, the above method may also include viewing a visual indicator presented by the test strip 108 through a viewing window 128, thereby indicating the presence of a substance under test.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the spirit and scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

We claim:

1. A testing device for collecting and testing a bodily fluid for a substance, the testing device comprising:
   a body assembly including a collection sponge;
   a cap assembly, including:
      a cap having a first end and a second end opposite the first end, and configured to receive a portion of a body assembly at the second end when the portion of body assembly is inserted into the cap, the cap defining a first cap cavity at the first end and a second cap cavity at the second end;
      a fluid container disposed in the first cap cavity, wherein the fluid container includes a sealing membrane and contains a mixing fluid for mixing with a bodily fluid; and
      a plunger with an end wall, the plunger being movably disposed in the second cap cavity, wherein the body assembly and the cap assembly are configured to interact such that relative axial movement of the cap from an earlier engagement position to a later engagement position will cause compression of the collection sponge by the end wall of the plunger.

2. The testing device of claim 1, wherein the plunger comprises a body portion extending from the end wall, the body portion having a tip, wherein the tip is spaced apart from the sealing membrane when the cap assembly is separated from the body assembly prior to use.

3. The testing device of claim 2, wherein the tip penetrates the sealing membrane of the fluid container when the plunger is in the earlier engagement position.

4. The testing device of claim 1, wherein the body assembly comprises a test strips channel configured to receive a mixture of the bodily fluid and the mixing fluid.

5. The testing device of claim 4, wherein the body assembly further comprises one or more test strips disposed in the test strips channel.

6. The testing device of claim 5, wherein the collection sponge is in fluid communication with the one or more test strips.

7. The testing device of claim 1, wherein when the cap receives a cap engagement portion of the body assembly.

8. The testing device of claim 1, wherein the body assembly and the cap assembly are configured such that the cap will be in a first angular orientation in the earlier engagement position and a second angular orientation in the later engagement position.

9. The testing device of claim 1, wherein a second side of the end wall of the plunger facing the second end of the cap will contact the compression sponge in the earlier engagement position with a first side of the end wall facing the first end of the cap.

10. The testing device of claim 7, wherein the cap engagement portion of the body assembly defines a plurality of channels configured to guide axial movement of the cap assembly.

11. The testing device of claim 10, wherein the plurality of channels includes at least one axial channel to guide an extension portion of the plunger and at least one configured channel to guide axial movement of the cap.

12. The testing device of claim 11, wherein the cap and plunger are configured such that the cap can move relative to the plunger in a rotational direction.

13. The testing device of claim 11, wherein the configured channel has a first axial channel portion, a second radial channel portion, and a third axial channel portion.

14. The testing device of claim 13, wherein the cap includes an inwardly directed alignment member operative to engage the configured channel of the cap engagement portion.

15. The testing device of claim 1, wherein the plunger further includes a plunger extension portion and a body portion of the body assembly further includes a cap-engagement portion for receiving the plunger extension portion.

16. The testing device of claim 15, wherein the body assembly and the cap assembly are configured such that the extension portion will engage a rim of the cap-engagement portion when the cap assembly is in an initial engagement position prior to the earlier engagement position.

17. The testing device of claim 1, wherein a body portion of the body assembly further includes a vent channel.

18. The testing device of claim 1, wherein the body assembly and the cap assembly are separated prior to use.

19. The testing device of claim 8, wherein the body assembly and the cap assembly are further configured such that the cap will be in a third angular orientation in an initial engagement position prior to the earlier engagement position.

20. A multi-stage, bodily-fluid collection and testing device for collecting and testing a bodily fluid for a substance, the testing device comprising:
   a body assembly, including:
      a body portion including a fluid flow path extending from a collection sponge cavity to a test strips channel;
      a collection sponge attached to the body portion in the collection sponge cavity for absorbing a bodily fluid from a donor; and
      one or more test strips for receiving the bodily fluid and presenting a visual indicator indicating the presence of a predetermined substance; and
   a cap assembly, including:
      a cap having a first closed end and a second open end, and configured to receive a portion of the body portion when the portion of the body assembly is inserted into the cap, the cap defining a cap cavity;
      a fluid container having a sealing membrane and containing a mixing fluid for mixing with the bodily fluid, the fluid container being housed within the cap cavity; and
      a plunger movably disposed in the cap cavity, wherein the plunger includes a piercing end, wherein the plunger is able to be moved from a first position to a second position, and wherein at the first position the piercing end is spaced apart from the sealing membrane, and at the second position the piercing end penetrates the sealing membrane, wherein the plunger is also configured to engage and compress the collection sponge.

21. The testing device of claim 20, wherein the plunger is configured to engage the collection sponge but the collection sponge is not compressed when the plunger is at the first position.

22. The testing device of claim 20, wherein the plunger is configured to engage the collection sponge and the plunger is at the second position when the collection sponge is compressed.

23. The testing device of claim 22, wherein the plunger is movable along with the cap relative to the body portion in order to cause compression of the collection sponge.

* * * * *

UNITED STATES PATENT AND TRADEMARK OFFICE
CERTIFICATE OF CORRECTION

| | | |
|---|---|---|
| PATENT NO. | : 12,214,345 B2 | Page 1 of 1 |
| APPLICATION NO. | : 17/403013 | |
| DATED | : February 4, 2025 | |
| INVENTOR(S) | : Kevin S. Fuller et al. | |

It is certified that error appears in the above-identified patent and that said Letters Patent is hereby corrected as shown below:

On the Title Page

Right column, in item (57) "ABSTRACT", Line 2, delete "that. is" and replace with --that is--

Right column, in item (57) "ABSTRACT", Line 6, delete "donor, A" and replace with --donor. A--

Right column, in item (57) "ABSTRACT", Line 9, delete "onto the 'body," and replace with --onto the body,--

On Page 2, left column, in item (57) "ABSTRACT", Line 2, delete "a. pair" and replace with --a pair--

In the Specification

In Column 1, Line 12, delete "2105," and insert --2015,--

In Column 9, Line 43, delete "or and" and insert --or/and--

In Column 12, Lines 14-15, delete "sub stance." and insert --substance.--

Signed and Sealed this
Eighth Day of July, 2025

Coke Morgan Stewart
*Acting Director of the United States Patent and Trademark Office*